United States Patent
Yao

(10) Patent No.: US 10,369,382 B2
(45) Date of Patent: Aug. 6, 2019

(54) BASE FOR NOVEL ACCELERATOR THERAPY DEVICE AND NOVEL ACCELERATOR THERAPY DEVICE

(71) Applicant: SUZHOU LINATECH MEDICAL SCIENCE AND TECHNOLOGY CO., LTD., Industry Park Suzhou, Jiangsu (CN)

(72) Inventor: Jonathan Yi Yao, Jiangsu (CN)

(73) Assignee: SUZHOU LINATECH MEDICAL SCIENCE AND TECHNOLOGY CO., LTD., Jiangsu (CN)

( * ) Notice: Subject to any disclaimer, the term of this patent is extended or adjusted under 35 U.S.C. 154(b) by 179 days.

(21) Appl. No.: 15/552,574

(22) PCT Filed: Apr. 12, 2016

(86) PCT No.: PCT/CN2016/079046
§ 371 (c)(1),
(2) Date: Aug. 22, 2017

(87) PCT Pub. No.: WO2017/012377
PCT Pub. Date: Jan. 26, 2017

(65) Prior Publication Data
US 2018/0043185 A1 Feb. 15, 2018

(30) Foreign Application Priority Data
Jul. 17, 2015 (CN) .......................... 2015 1 0423148

(51) Int. Cl.
*A61N 5/10* (2006.01)

(52) U.S. Cl.
CPC ......... *A61N 5/1042* (2013.01); *A61N 5/1037* (2013.01); *A61N 5/1082* (2013.01); *A61N 5/1001* (2013.01); *A61N 5/1049* (2013.01)

(58) Field of Classification Search
CPC .. A61N 5/1001; A61N 5/1037; A61N 5/1042; A61N 5/1049; A61N 5/1082
See application file for complete search history.

(56) References Cited

U.S. PATENT DOCUMENTS 3,349,242 A * 10/1967 Braestrup ................ A61N 5/01
378/196
4,150,297 A * 4/1979 Borggren ............. A61B 6/4464
378/181

(Continued)

FOREIGN PATENT DOCUMENTS

CN 201019757 Y 2/2008
CN 202620492 U 12/2012
(Continued)

*Primary Examiner* — Marcus H Taningco
(74) *Attorney, Agent, or Firm* — Muncy, Geissler, Olds & Lowe, P.C.

(57) ABSTRACT

The invention discloses a base for a novel accelerator therapy device. A boat-shaped rocker arm is creatively utilized to drive a main frame to rotate around an X axis, and meanwhile an accelerator simultaneously follows the main frame to rotate around a Z axis, so that the accelerator runs on a spherical surface and irradiates an isocentric lesion in any direction of a three-dimensional spherical space; the center of gravity of the boat-shaped rocker arm is low, the boat-shaped rocker arm bears weight on the curved surface, and a rotating shaft and an upright post for bearing the weight of the main frame and the weight of the accelerator in the prior art are removed, so that the base is high in stability, safe, reliable and low in requirement for transmission equipment and easily realizes industrialized application.

10 Claims, 2 Drawing Sheets

(56) References Cited

U.S. PATENT DOCUMENTS

| | | | | |
|---|---|---|---|---|
| 8,303,181 B2 * | 11/2012 | Sukovic | ............... | A61B 6/032 378/197 |
| 8,664,618 B2 * | 3/2014 | Yao | .................... | A61N 5/1082 250/393 |
| 2004/0013239 A1 * | 1/2004 | Gregerson | .............. | A61B 6/02 378/197 |
| 2014/0171725 A1 * | 6/2014 | Adler | ...................... | G21F 3/00 600/1 |
| 2015/0190658 A1 * | 7/2015 | Yu | ......................... | A61N 5/10 600/1 |
| 2015/0238159 A1 * | 8/2015 | Al Assad | ............ | A61B 6/5258 378/5 |
| 2016/0095558 A1 * | 4/2016 | Choy | ................. | A61B 6/0407 600/407 |

FOREIGN PATENT DOCUMENTS

| | | |
|---|---|---|
| CN | 204890990 U | 12/2015 |
| JP | 2014128412 A | 7/2014 |
| WO | WO 2015103564 A1 | 7/2015 |

\* cited by examiner

BASE FOR NOVEL ACCELERATOR THERAPY DEVICE AND NOVEL ACCELERATOR THERAPY DEVICE

FIELD OF THE INVENTION

The present invention relates to an accelerator therapy device, and specifically relates to a base for a novel accelerator therapy device and the novel accelerator therapy device.

BACKGROUND OF THE INVENTION

With the development of tumor radiology and material science, radiotherapy has gradually entered the age of "three precisions" comprising precise positioning, precise planning and precise therapy as an important means for treating cancers. When the rotating plane of a main frame is set to be perpendicular to the horizontal plane, the rotating plane is an X plane, its rotating axis at the moment is defined as a Z axis, the horizontal straight line perpendicular to and cross with the Z axis is an X axis, and the straight line perpendicular to and cross with the Z axis and the X axis respectively is a Y axis. The Z axis and the Y axis define a Y plane, the Y axis and the X axis define an X plane, and the Z axis and the X axis define a horizontal plane (Z plane). The present medical linear accelerator (radiotherapy equipment) is driven by rotation of the main frame to rotate in the X plane or a plane parallel to the X plane, the accelerator follows the main frame to rotate, and the central axis of rays emitted by the accelerator is perpendicular to the rotating axis of the main frame and is intersected with the rotating axis at a point, i.e., an isocenter. Generally, during therapy, the lesion of a patient is put at the isocenter, the main frame is rotated, the accelerator rotates around the lesion in the X plane or the plane parallel to the X plane, and thus rays irradiate the lesion from different directions to better kill sick cells. However, both the patient and the lesion have a three-dimensional size, and the present therapy equipment can only irradiate 360° from one planar space, but cannot irradiate a three-dimensional spherical space. Thus, a so-called accelerator nodding device is emerged, which is mainly characterized in that the main frame is suspended on two struts via a rotating shaft on the X axis, and a driving device drives the main frame to rotate around the X axis; the main frame and the accelerator are very heavy, and the torque borne by the rotating shaft is very large, so the requirement for the driving device is very high.

SUMMARY OF THE INVENTION

In order to solve the above problems, the present invention is aimed at providing a base for a novel accelerator therapy device and the novel accelerator therapy device, wherein the accelerator runs on a spherical surface in a three-dimensional manner, thereby irradiating a lesion in any direction of the three-dimensional space (isocenter).

To fulfill the above aim, the present invention adopts the technical solution:

a base for a novel accelerator therapy device is used for the accelerator therapy device, the accelerator therapy device comprises a therapy control device, a main frame and an accelerator, the accelerator is installed on the main frame, the therapy control device is used for controlling the accelerator and the main frame, and the base for the novel accelerator therapy device comprises:

a boat-shaped rocker arm, wherein the main frame is installed at the upper part of the boat-shaped rocker arm, the lower part of the boat-shaped rocker arm is an arc curved surface, and the boat-shaped rocker arm can rotate around a circle center corresponding to the arc curved surface; the main frame can rotate around an axis, the accelerator follows the main frame to rotate, and the central axis of rays emitted by the accelerator is perpendicular to the axis and is intersected with the axis at a point, i.e., an isocenter; the rotating plane of the boat-shaped rocker arm is perpendicular to that of the main frame; the circle center is superposed with the isocenter; the accelerator runs on a spherical surface under the co-action of rotation of the boat-shaped rocker arm and rotation of the main frame, the sphere center of the spherical surface is the isocenter, and the sphere center is located on the central axis of rays emitted by the accelerator all the time; and a driving device, which is in transmission connection with the boat-shaped rocker arm and drives the boat-shaped rocker arm to rotate around the circle center corresponding to the arc curved surface.

The boat-shaped rocker arm drives the main frame to rotate around an X axis, and the accelerator simultaneously follows the main frame to rotate around a Z axis, so that the accelerator runs on a spherical surface and irradiates an isocentric lesion in any direction of a three-dimensional spherical space; the center of gravity of the boat-shaped rocker arm is low, the boat-shaped rocker arm bears weight on the curved surface, and a rotating shaft and an upright post for bearing the weight of the main frame and weight of the accelerator in the prior art are removed, so that the base is high in stability, safe, reliable and low in requirement for transmission equipment and easily realizes industrialized application.

Further, the driving device comprises:

a plurality of supporting rollers arranged around the arc curved surface, wherein the supporting rollers are used for supporting the boat-shaped rocker arm as well as the main frame and the accelerator thereon;

a support frame, wherein the supporting rollers are installed on the support frame, and the support frame is installed on the ground or a horizontal foundation; and a driving assembly, comprising a motor and a deceleration device having an input end in transmission connection with the motor, wherein the output end of the deceleration device is in transmission connection with one or a few of the supporting rollers, and the motor drives the one or a few of the supporting rollers to rotate reciprocally through the deceleration device, thereby driving the boat-shaped rocker arm to rotate reciprocally; or, transmission convex teeth are arranged on the arc curved surface of the bottom of the boat-shaped rocker arm and engaged with a driving gear in a transmission manner, the driving gear is in transmission connection with the output end of the deceleration device, and the motor drives the driving gear to rotate reciprocally through the deceleration device, thereby driving the boat-shaped rocker arm to rotate reciprocally.

The boat-shaped rocker arm is supported by the supporting rollers, the supporting rollers are arranged along the arc curved surface at the lower part of the boat-shaped rocker arm to form multi-point support, and the supporting rollers simultaneously have three effects: I, supporting; II, reducing the rotating resistance of the boat-shaped rocker arm; and III, removing a rotating shaft for the boat-shaped rocker arm, i.e., the boat-shaped rocker arm rotates reciprocally around a fixed axis (an isocenter or referred to as a sphere center) without a rotating shaft. The supporting rollers are directly fixedly installed on the ground or a pedestal via respective rotating shafts, and the weight of the whole equipment is shared by the plurality of rotating shafts, so that the requirement for the rotating shafts is greatly reduced; the center of gravity of the whole equipment is low, and the boat-shaped rocker arm is held and supported by the plurality of supporting rollers, so that the posture of the whole equipment is controlled more easily, and the possible safety risk of the traditional rotating shaft suspension solution is also solved; in the traditional rotating shaft suspension solution, the rotating shafts must be very thick and strong, otherwise, there is the risk of shaft breakage overturn, besides, the requirement for bearings is also very high, and meanwhile, the requirements for reliability of a braking device and high power of the driving device greatly increase the manufacturing cost.

Further, the main frame is installed on one side of the upper part of the boat-shaped rocker arm, and a balancing weight assembly for balancing the weight of the main frame and the weight of the accelerator is installed on the other side of the boat-shaped rocker arm.

The connecting lines between two end points of the arc curved surface of the boat-shaped rocker arm and the isocenter (circle center or sphere center) and the arc curved surface jointly constitute a sector, the connecting line between the two end points constitutes an upper platform of the boat-shaped rocker arm, the main frame is installed on one side, close to one end point, of the platform, and the balancing weight assembly equivalent to the total weight of the main frame, the accelerator and other component is assembled inside the boat-shaped rocker arm on the other side or assembled at the upper part of the platform close to the end point according to needs, the whole device is thus in a balanced state in case of no external force interference, the main frame at the moment is in a state of being perpendicular to the horizontal plane, and the axes of rays emitted by the accelerator are also perpendicular to the horizontal plane. By arranging the balancing weight assembly, the requirement for power of the driving device and the requirement for a locking and limiting device are greatly reduced, the manufacturing cost is greatly reduced, and a better support is provided for industrialized application.

Further, the driving device comprises:
the support frame comprising:
a chain structure of a plurality of rotating shafts, the supporting rollers being installed on the rotating shafts respectively;
supporting plates, each rotating shaft being correspondingly installed between a pair of supporting plates, and the supporting plates being installed on supporting seats; and
the supporting seats, the supporting seats being installed on the ground or the horizontal foundation.

The chain structure enables the rotating shafts of all the supporting rollers to be connected by the connecting plates (similar to connecting plates of a chain), which is equivalent to increasing a transverse stabilization system, thereby greatly improving the stability of each supporting roller, and reducing the risk of deformation of a supporting assembly (e.g., the supporting plate and the supporting seat in this solution) for the single supporting roller under the extreme situation.

Further, the driving device comprises:
the supporting seats comprising one middle supporting seat and side supporting seats on two sides of the middle supporting seat, and each side supporting seat having a slope, so that the supporting rollers correspondingly installed thereon contact the arc curved surface of the boat-shaped rocker arm, wherein the connecting line between each of the contact point and the rotating axis of the corresponding supporting roller is perpendicular to the slope.

By such setting, each group of supporting rollers and supporting assemblies thereof are stressed consistently as their axes, thereby avoiding deformation damage of transverse torque to the supporting assemblies.

Further, the driving device comprises:
the side supporting seats being installed on a slide rail, two pre-tightening adjusting devices being also arranged on the slide rail, the two pre-tightening adjusting devices being respectively located outside the two side supporting seats, and the pre-tightening adjusting devices driving the side supporting seats to move back and forth on the slide rail.

In this device, the contact between the supporting rollers on two sides and the arc curved surface can be conveniently adjusted to an optimal state.

Further, there is one boat-shaped rocker arm or a pair of boat-shaped rocker arms.

When there is one boat-shaped rocker arm, it can be arranged below the central axis of the main frame or biased on one side, and when it is biased on one side, the requirements for strength and stability of the whole system are very high; two boat-shaped rocker arms may also be symmetrically arranged on two sides of the central axis, and the boat-shaped rocker arms can be arranged under the basic plane of a workbench in a semi-buried or fully-buried manner, thereby reducing the influence on the working environment.

The present invention further provides a novel accelerator therapy device, comprising a therapy control device, a main frame, an accelerator and a base for the novel accelerator therapy device, wherein the accelerator is installed on the main frame, the therapy control device controls the accelerator and the main frame, and the base for the novel accelerator therapy device comprises:

a boat-shaped rocker arm, wherein the main frame is installed at the upper part of the boat-shaped rocker arm, the lower part of the boat-shaped rocker arm is an arc curved surface, and the boat-shaped rocker arm can rotate around a circle center corresponding to the arc curved surface; the main frame can rotate around an axis, the accelerator follows the main frame to rotate, and the central axis of rays emitted by the accelerator is perpendicular to the axis and is intersected with the axis at a point, i.e., an isocenter; the rotating plane of the boat-shaped rocker arm is perpendicular to that of the main frame; the circle center is superposed with the isocenter; the accelerator runs on a spherical surface under the co-action of rotation of the boat-shaped rocker arm and rotation of the main frame, the sphere center of the spherical surface is the isocenter, and the sphere center is located on the central axis of rays emitted by the accelerator all the time; and a driving device, which is in transmission connection with the boat-shaped rocker arm and drives the boat-shaped rocker arm to rotate around the circle center corresponding to the arc curved surface.

Further, the main frame is installed on one side of the upper part of the boat-shaped rocker arm, and a balancing weight assembly for balancing the weight of the main frame and the weight of the accelerator is installed on the other side of the boat-shaped rocker arm.

Further, the base for the novel accelerator therapy device is any above-mentioned one.

Figure 1:
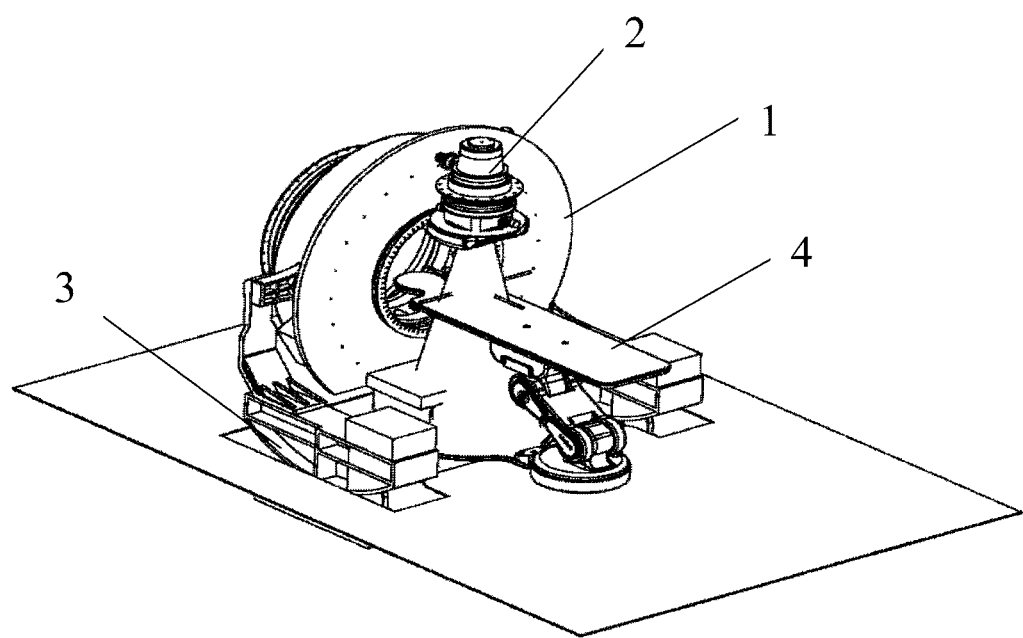
FIGS. 1 and 2 are schematic diagrams of the present invention.

Numbers and letters in the drawings express corresponding components:

1, main frame; 2, accelerator; 3, boat-shaped rocker arm; 4, therapy bed; 31, supporting roller; 5, isocenter; 6, rotating axis; 32, supporting plate; 34, supporting seat; 35, pre-tightening adjusting device; 33, safety device.

DETAILED DESCRIPTION OF THE EMBODIMENTS

The present invention will be further described in detail below in combination with the accompanying drawings and specific embodiments.

In one embodiment of the present invention, as shown in FIG. 1, in order to fulfill the above aim, the present invention adopts the following technical solution:

a base for a novel accelerator therapy device is used for the accelerator therapy device, the accelerator therapy device comprises a therapy control device (not shown in the figure), a main frame 1 and an accelerator 2, the accelerator 2 is installed on the main frame 1, the therapy control device controls the accelerator 2 and the main frame 1, and the base for the novel accelerator therapy device comprises:

a boat-shaped rocker arm 3, wherein the main frame 1 is installed at the upper part of the boat-shaped rocker arm 3, the lower part of the boat-shaped rocker arm 3 is an arc curved surface, and the boat-shaped rocker arm 3 can rotate around the circle center corresponding to the arc curved surface; the main frame 1 can rotate around an axis, the accelerator 2 follows the main frame to rotate, and the central axis of rays emitted by the accelerator 2 is perpendicular to the rotating axis of the main frame and is intersected with the axis at a point, i.e., an isocenter; the rotating plane of the boat-shaped rocker arm 3 is perpendicular to that of the main frame 1; the circle center is superposed with the isocenter; the accelerator 2 runs on a spherical surface under the co-action of rotation of the boat-shaped rocker arm 3 and rotation of the main frame 1, the sphere center of the spherical surface is the isocenter, and the sphere center is located on the central axis of rays emitted by the accelerator all the time; and a driving device, which is in transmission connection with the boat-shaped rocker arm 3 and drives the boat-shaped rocker arm 3 to rotate around the circle center corresponding to the arc curved surface.

The boat-shaped rocker arm 3 drives the main frame to rotate around an X axis (i.e., the rotating axis of the boat-shaped rocker arm), and meanwhile the accelerator 2 follows the main frame 1 to rotate around a Z axis (i.e., the rotating axis of the main frame itself); specifically, the rotating center of the boat-shaped rocker arm is superposed with the isocenter, and no matter when the boat-shaped rocker arm rotates, the main frame follows the boat-shaped rocker arm to rotate or the main frame rotates per se, the position of the isocenter is fixed, so that the accelerator 2 runs on a spherical surface and irradiates an isocentric lesion in any direction of a three-dimensional spherical space; the center of gravity of the boat-shaped rocker arm 3 is low, the boat-shaped rocker arm 3 bears weight on the curved surface, and a rotating shaft and an upright post for bearing the weight of the main frame 1 and the weight of the accelerator 2 in the prior art are removed, so that the base is high in stability, safe, reliable and low in requirement for transmission equipment and easily realizes industrialized application.

Figure 2:
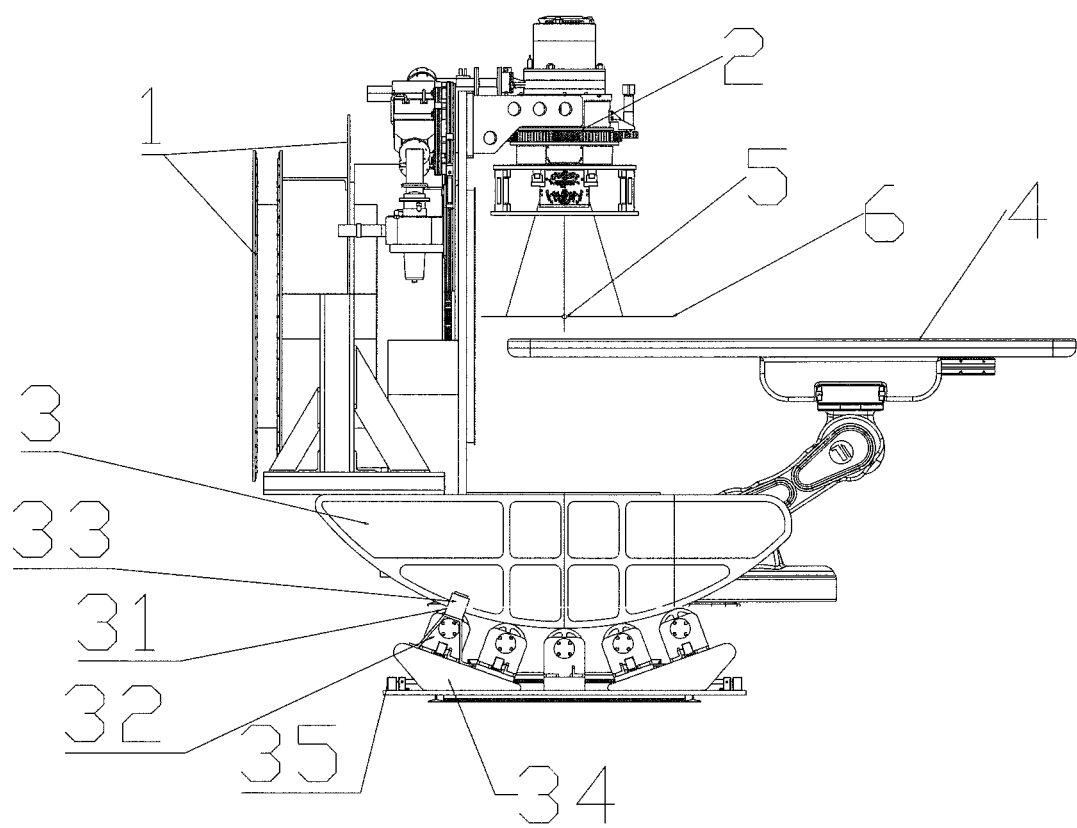

In practical application, in order to realize that the boat-shaped rocker arm rotates around the isocenter, in one embodiment, as shown in FIG. 2, the driving device comprises:

a plurality of supporting rollers 31 arranged around the arc curved surface, wherein the supporting rollers 31 are used for supporting the boat-shaped rocker arm 3 as well as the main frame 1 and the accelerator 2 thereon;

a support frame, wherein the supporting rollers 31 are installed on the support frame, and the support frame is installed on the ground or a horizontal foundation;

a driving assembly, comprising a motor and a deceleration device having an input end in transmission connection with the motor, wherein the output end of the deceleration device is in transmission connection with one or a few of the supporting rollers 31, and the motor drives the one or a few of the supporting rollers 31 to rotate reciprocally through the deceleration device, thereby driving the boat-shaped rocker arm 3 to rotate reciprocally; or, transmission convex teeth are arranged on the arc curved surface of the bottom of the boat-shaped rocker arm 3 and engaged with a driving gear in a transmission manner, the driving gear is in transmission connection with the output end of the deceleration device, and the motor drives the driving gear to rotate reciprocally through the deceleration device, thereby driving the boat-shaped rocker arm 3 to rotate reciprocally. At the moment, the supporting rollers 31 only achieve the effects of supporting and reducing resistance.

The boat-shaped rocker arm 3 is supported by the supporting rollers 31, the supporting rollers are arranged along the arc curved surface at the lower part of the boat-shaped rocker arm 3 to form multi-point support, and the supporting rollers 31 simultaneously have three effects: I, supporting; II, reducing the rotating resistance of the boat-shaped rocker arm 3; and III, removing a rotating shaft for the boat-shaped rocker arm 3, i.e., the boat-shaped rocker arm rotates reciprocally around a fixed axis (the rotating axis of the boat-shaped rocker arm is vertically intersected with the rotating axis 6 of the main frame 1, and this intersection is an isocenter 5 or referred to as a sphere center) without a rotating shaft. The supporting rollers 31 are directly fixedly installed on the ground or a pedestal via respective rotating shafts, and the weight of the whole equipment is shared by the plurality of rotating shafts, so that the requirement for the rotating shafts is greatly reduced; the center of gravity of the whole equipment is low, and the boat-shaped rocker arm 3 is held and supported by the plurality of supporting rollers 31, so that the posture of the whole equipment is controlled more easily, and the possible safety risk of the traditional rotating shaft suspension solution is also solved; in the traditional rotating shaft suspension solution, the rotating shafts must be very thick and strong, otherwise, there is the risk of shaft breakage and overturn, besides, the requirement for bearings is also very high, and meanwhile, the requirements for reliability of a braking device and high power of the driving device greatly increase the manufacturing cost.

In order to further optimize the above solution, the main frame is installed on one side of the upper part of the boat-shaped rocker arm 3, and a balancing weight assembly for balancing the weight of the main frame 1 and the weight of the accelerator 2 is installed on the other side of the boat-shaped rocker arm 3. In this case, the requirement for power of the driving assembly can be greatly reduced, the manufacturing cost and the operating cost are reduced, and the base is energy-saving and environment-friendly.

Specifically, the connecting lines between two end points of the arc curved surface of the boat-shaped rocker arm 3 and the isocenter 5 (circle center or sphere center) and the arc curved surface jointly constitute a sector, the connecting line between the two end points constitutes an upper platform of the boat-shaped rocker arm 3, the main frame 1 is installed on one side, close to one end point, of the platform, the balancing weight assembly equivalent to the total weight of the main frame 1, the accelerator 2 and other component is assembled inside the boat-shaped rocker arm 3 on the other side or assembled at the upper part of the platform close to the end point according to needs, the whole device is thus in a balanced state in case of no external force interference, the main frame 1 at the moment is in a state of being perpendicular to the horizontal plane, and the axes of rays emitted by the accelerator 2 are also perpendicular to the horizontal plane. By arranging the balancing weight assembly, the requirement for power of the driving device and the requirement for a locking and limiting device are greatly reduced, the manufacturing cost is greatly reduced, and a better support is provided for industrialized application.

In some other embodiments, the driving device is further optimized, and comprises:

the support frame comprising:

a chain structure of a plurality of rotating shafts, the adjacent rotating shafts being connected by a connecting plate, the supporting rollers being installed on the corresponding rotating shafts respectively, and the chain structure being similar to a chain;

supporting plates 32, each rotating shaft being correspondingly installed between a pair of supporting plates, and the supporting plates being installed on supporting seats; and the supporting seats 34, the supporting seats being installed on the ground or the horizontal foundation.

The chain structure enables the rotating shafts of all the supporting rollers to be connected by the connecting plates (similar to connecting plates of a chain), which is equivalent to increasing a transverse stabilization system, thereby greatly improving the stability of each supporting roller, and reducing the risk of deformation of a supporting assembly (e.g., the supporting plate and the supporting seat in this solution) for the single supporting roller under the extreme situation.

In a specific embodiment, the supporting seats 34 can be further optimized, and the driving device comprises:

the supporting seats comprising one middle supporting seat 34 and side supporting seats on two sides of the middle supporting seat, and each side supporting seat having a slope, so that the supporting rollers correspondingly installed thereon contact the arc curved surface of the boat-shaped rocker arm, wherein the connecting line between each of the contact points and the rotating axis of the corresponding supporting roller is perpendicular to the slope.

By such setting, each group of supporting rollers and supporting assemblies thereof are stressed consistently as their axes, thereby avoiding deformation damage of transverse torque to the supporting assemblies.

Further, the driving device comprises:

the side supporting seats being installed on a slide rail, two pre-tightening adjusting devices 35 being also arranged on the slide rail, the two pre-tightening adjusting devices 35 being respectively located outside the two side supporting seats, and the pre-tightening adjusting devices driving the side supporting seats to move back and forth on the slide rail.

In this device, the contact between the supporting rollers 31 on two sides and the arc curved surface can be conveniently adjusted to an optimal state.

In practical application, in order to realize that the boat-shaped rocker arm 3 runs more safely and reliably, a safety device 33 is arranged, the arc curved surface of the boat-shaped rocker arm 3 extends to two sides (or is sunken) to form an arc upper curved surface, and a group of rollers arranged for the safety device 33 presses the upper curved surface and clamps the boat-shaped rocker arm together with the supporting rollers, so that the boat-shaped rocker arm does not shake or vibrate and the boat-shaped rocker arm is conveniently locked at any position. A cantilever of the safety device 33 is fixedly connected with the supporting seats or the ground foundation.

Further, there is one boat-shaped rocker arm or a pair of boat-shaped rocker arms.

When there is one boat-shaped rocker arm, it can be arranged below the central axis of the main frame or biased on one side, and when it is biased on one side, the requirements for strength and stability of the whole system are very high; the therapy bed 4 at the moment can be supported by a suspended mechanical arm to avoid interference. Two boat-shaped rocker arms may also be symmetrically arranged on two sides of the central axis, and the boat-shaped rocker arms can be arranged under the basic plane of a workbench in a semi-buried or fully-buried manner, thereby reducing the influence on the working environment. The therapy bed 4 at the moment is arranged at a position between the two boat-shaped rocker arms, and may also be supported by a mechanical arm.

The present invention further provides a novel accelerator therapy device, comprising a therapy control device, a main frame, an accelerator and the aforesaid base for the novel accelerator therapy device.

Described above are merely preferred embodiments of the present invention. It should be pointed out that many modifications and improvements can also be made for those of ordinary skill in the art without departing from the concept of the present invention. These modifications and improvements shall fall into the protection scope of the present invention.

The invention claimed is:

1. A base for a novel accelerator therapy device, which is used for the accelerator therapy device comprising a therapy control device, a main frame and an accelerator, wherein the accelerator is installed on the main frame, the therapy control device is used for controlling the accelerator and the main frame, and the base for the novel accelerator therapy device comprises:

a boat-shaped rocker arm, wherein the main frame is installed at the upper part of the boat-shaped rocker arm, the lower part of the boat-shaped rocker arm is an arc curved surface, and the boat-shaped rocker aim can rotate around a circle center corresponding to the arc curved surface; the main frame can rotate around an axis, the accelerator follows the main frame to rotate, and the central axis of rays emitted by the accelerator is perpendicular to the axis and is intersected with the axis at a point, i.e., an isocenter; the rotating plane of the boat-shaped rocker arm is perpendicular to that of the main frame; the circle center is superposed with the isocenter; the accelerator runs on a spherical surface under the co-action of rotation of the boat-shaped rocker arm and rotation of the main frame, and the sphere center of the spherical surface is the isocenter, and the sphere center is located on the central axis of rays emitted by the accelerator all the time; and a driving device, which is in transmission connection with the boat-shaped rocker arm and drives the boat-shaped rocker arm to rotate around the circle center corresponding to the arc curved surface.

2. The base for a novel accelerator therapy device according to claim 1, wherein the driving device comprises:
   a plurality of supporting rollers arranged around the arc curved surface, wherein the supporting rollers are used for supporting the boat-shaped rocker arm as well as the main frame and the accelerator thereon;
   a support frame, wherein the supporting rollers are installed on the support frame, and the support frame is installed on the ground or a horizontal foundation; and
   a driving assembly, comprising a motor and a deceleration device having an input end in transmission connection with the motor, wherein the output end of the deceleration device is in transmission connection with one or a few of the supporting rollers, and the motor drives the one or a few of the supporting rollers to rotate reciprocally through the deceleration device, thereby driving the boat-shaped rocker arm to rotate reciprocally; or, transmission convex teeth are arranged on the arc curved surface of the bottom of the boat-shaped rocker arm and engaged with a driving gear in a transmission manner, the driving gear is in transmission connection with the output end of the deceleration device, and the motor drives the driving gear to rotate reciprocally through the deceleration device, thereby driving the boat-shaped rocker arm to rotate reciprocally.

3. The base for a novel accelerator therapy device according to claim 1, wherein the main frame is installed on one side of the upper part of the boat-shaped rocker arm, and a balancing assembly for balancing the weight of the main frame and the weight of the accelerator is installed on the other side of the boat-shaped rocker arm.

4. The base for a novel accelerator therapy device according to claim 2, wherein the driving device comprises:
   the support frame comprising:
   a chain structure of a plurality of rotating shafts, the supporting rollers being installed on the rotating shafts respectively;
   supporting plates, each rotating shaft being correspondingly installed between a pair of supporting plates, and the supporting plates being installed on supporting seats; and
   the supporting seats, the supporting seats being installed on the ground or the horizontal foundation.

5. The base for a novel accelerator therapy device according to claim 4, wherein the driving device comprises:
   the supporting seats comprising one middle supporting seat and side supporting seats on two sides of the middle supporting seat, and each side supporting seat having a slope, so that the supporting rollers correspondingly installed thereon contact the arc curved surface of the boat-shaped rocker arm, wherein the connecting line between each of the contact points and the rotating axis of the corresponding supporting roller is perpendicular to the slope.

6. The base for a novel accelerator therapy device according to claim 5, wherein the driving device comprises:
   the side supporting seats being installed on a slide rail, two pre-tightening adjusting devices being also arranged on the slide rail, the two pre-tightening adjusting devices being respectively located outside the two side supporting seats, and the pre-tightening adjusting devices driving the side supporting seats to move back and forth on the slide rail.

7. The base for a novel accelerator therapy device according to claim 1, wherein there is one boat-shaped rocker arm or a pair of boat-shaped rocker arms.

8. A novel accelerator therapy device, comprising a therapy control device, a main frame, an accelerator and a base for the novel accelerator therapy device, wherein the accelerator is installed on the main frame, the therapy control device controls the accelerator and the main frame, and the base for the novel accelerator therapy device comprises:
   a boat-shaped rocker aim, wherein the main frame is installed at the upper part of the boat-shaped rocker arm, the lower part of the boat-shaped rocker arm is an arc curved surface, and the boat-shaped rocker arm can rotate around the circle center corresponding to the arc curved surface; the main frame can rotate around an axis, the accelerator follows the main frame to rotate, and the central axis of rays emitted by the accelerator is perpendicular to the axis and is intersected with the axis at a point, i.e., an isocenter; the rotating plane of the boat-shaped rocker arm is perpendicular to that of the main frame; the circle center is superposed with the isocenter; the accelerator runs on a spherical surface under the co-action of rotation of the boat-shaped rocker arm and rotation of the main frame, the sphere center of the spherical surface is the isocenter, and the sphere center is located on the central axis of rays emitted by the accelerator all the time; and
   a driving device, which is in transmission connection with the boat-shaped rocker arm and drives the boat-shaped rocker arm to rotate around the circle center corresponding to the arc curved surface.

9. The novel accelerator therapy device according to claim 8, wherein the main frame is installed on one side of the upper part of the boat-shaped rocker arm, and a balancing weight assembly for balancing the weight of the main frame and the weight of the accelerator is installed on the other side of the boat-shaped rocker arm.

10. The novel accelerator therapy device according to claim 8, wherein the base for the novel accelerator therapy device comprises:
   a plurality of supporting rollers arranged around the arc curved surface, wherein the supporting rollers are used for supporting the boat-shaped rocker arm as well as the main frame and the accelerator thereon;
   a support frame, wherein the supporting rollers are installed on the support frame, and the support frame is installed on the ground or a horizontal foundation; and
   a driving assembly, comprising a motor and a deceleration device having an input end in transmission connection with the motor, wherein the output end of the deceleration device is in transmission connection with one or a few of the supporting rollers, and the motor drives the one or a few of the supporting rollers to rotate reciprocally through the deceleration device, thereby driving the boat-shaped rocker arm to rotate reciprocally; or, transmission convex teeth are arranged on the arc curved surface of the bottom of the boat-shaped rocker arm and engaged with a driving gear in a transmission manner, the driving gear is in transmission connection with the output end of the deceleration device, and the motor drives the driving gear to rotate reciprocally through the deceleration device, thereby driving the boat-shaped rocker arm to rotate reciprocally.

\* \* \* \* \*